( 12 ) United States Patent
Martinez Gutierrez et al.

(10) Patent No.: US 12,319,951 B2
(45) Date of Patent: *Jun. 3, 2025

(54) ENZYMATICALLY SYNTHESIZED OMEGA-3 STRUCTURED PHOSPHOLIPIDS

(71) Applicants: Wilson Martinez Gutierrez, Barranquilla (CO); Alvaro Jose Garcia Padilla, Barranquilla (CO); Alfredo de Jesús Puche Simanca, Barranquilla (CO); Tatiana Lucia Yepes Bustillo, Barranquilla (CO)

(72) Inventors: Wilson Martinez Gutierrez, Barranquilla (CO); Alvaro Jose Garcia Padilla, Barranquilla (CO); Alfredo de Jesús Puche Simanca, Barranquilla (CO); Tatiana Lucia Yepes Bustillo, Barranquilla (CO)

(73) Assignee: C.I. Naturmega S.A., Barranquilla (CO)

( * ) Notice: Subject to any disclaimer, the term of this patent is extended or adjusted under 35 U.S.C. 154(b) by 0 days.

This patent is subject to a terminal disclaimer.

(21) Appl. No.: 17/951,048

(22) Filed: Sep. 22, 2022

(65) Prior Publication Data

US 2023/0091294 A1    Mar. 23, 2023

Related U.S. Application Data

(60) Provisional application No. 63/246,898, filed on Sep. 22, 2021.

(51) Int. Cl.
*C12P 19/44*    (2006.01)
*C12P 13/00*    (2006.01)

(52) U.S. Cl.
CPC .............. *C12P 19/44* (2013.01); *C12P 13/001* (2013.01)

(58) Field of Classification Search
CPC ........ A23L 33/12; C12P 19/44; C12P 7/6481; C12P 7/6472; C12P 7/6458; C12P 7/6436; A61K 47/544; A23D 7/0053
USPC .......................................................... 435/74
See application file for complete search history.

(56) References Cited

PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*

* cited by examiner

*Primary Examiner* — Robert B Mondesi
*Assistant Examiner* — Mohammad Y Meah
(74) *Attorney, Agent, or Firm* — Isaac Angres

(57) ABSTRACT

The invention provides a process of incorporation of omega-3 fatty acids such as EPA/DHA into polar lipid molecules present in lecithin, which consists of: (a) an enzymatic exchange reaction between the fatty acids present in the polar lipids of lecithin and the omega-3 fatty acids present in concentrated fish oil, to obtain an oil with a high content of polar lipids and omega-3 fatty acids and (b) a stage of concentration of the polar lipid content of the oil obtained in stage a, by supercritical fractionation or molecular distillation.

14 Claims, 8 Drawing Sheets

ENZYMATICALLY SYNTHESIZED OMEGA-3 STRUCTURED PHOSPHOLIPIDS

This application claims the priority benefit under 35 U.S.C. section 119 of U.S. Provisional Patent Application No. 63/246,898 entitled "Enzymatically Synthesized Omega-3 Structured Phospholipids" filed on Sep. 22, 2021; and which is in its entirety herein incorporated by reference.

FIELD OF THE INVENTION

The invention relates to the production of phospholipid and glycolipids preparations which are enriched with omega-3 and omega-6 fatty acids. The omega-3 and omega-6-enriched phospholipid and glycolipid preparations produced by the methods of the invention can be used as nutraceuticals or nutraceutical additives to functional foods or pharmaceutical compositions. The present invention further relates to an enzymatic process for the preparation of phospholipid having incorporated therein omega-3 and omega-6 fatty acids.

BACKGROUND OF THE INVENTION

Phospholipids are an important class of biomolecules. Phospholipids are the fundamental building blocks of cellular membranes and are the major part of surfactant, the film that occupies the air/liquid interfaces in the lung. These molecules consist of a polar or charged head group and a pair of nonpolar fatty acid tails, connected via a glycerol linkage. This combination of polar and nonpolar segments is termed amphiphilic, and the word describes the tendency of these molecules to assemble at interfaces between polar and nonpolar phases.

The term glycerophospholipid signifies any derivative of glycerophosphoric acid that contains at least one O-acyl, or O-alkyl, or O-alk-1'-enyl residue attached to the glycerol moiety. The phosphate group forms an ester linkage to the glycerol. The long-chained hydrocarbons are typically attached through ester linkages in bacteria/eucaryotes.

In bacteria and procaryotes, the lipids consist of diesters commonly of $C_{16}$ or $C_{18}$ fatty acids. These acids are straight-chained and, especially for the $C_{18}$ members, can be unsaturated. Hydrocarbon chains attached to the glycerol are hydrophobic while the polar head, which mainly consists of the phosphate group attached to the third carbon of the glycerol backbone, is hydrophilic. This dual characteristic leads to the amphipathic nature of glycerophospholipids. They are usually organized into a bilayer in membranes with the polar hydrophilic heads sticking outwards to the aqueous environment and the non-polar hydrophobic tails pointing inwards. Glycerophospholipids consist of various diverse species which usually differ slightly in structure. The most basic structure is a phosphatidate. This species is an important intermediate in the synthesis of many phosphoglycerides.

In general, glycerophospholipids use a "sn" notation, which stands for stereospecific numbering. When the letters "sn" appear in the nomenclature, by convention the hydroxyl group of the second carbon of glycerol (2-sn) is on the left on a Fischer projection. The numbering follows the one of Fischer's projections, being 1-sn the carbon at the top and 3-sn the one at the bottom. The advantage of this particular notation is that the spatial configuration (D or L) of the glycero-molecule is determined intuitively by the residues on the positions sn-1 and sn-3. For example sn-glycero-3-phosphoric acid and sn-glycero-1-phosphoric acid are enantiomers. Most vegetable oils have unsaturated fatty acids in the sn-2 position, with saturated fatty acids in the 1-sn and/or 3-sn position. Animal fats more often have saturated fatty acids in the 2-sn, with unsaturated fatty acids in the 1-sn and/or sn3 position.

Phospholipids containing poly-unsaturated fatty acids (PUFA) supply the organism with important building blocks which improve membrane fluidity, an essential property for the function of biological membranes.

Studies conducted with PUFA containing phospholipids have shown that these biomaterials have many important physiological roles. They are highenergy, basic, structural, and functional elements of all biological membranes such as cells, blood corpuscles, lipoproteins, and the surfactant. Furthermore, they are indispensable for cellular differentiation, proliferation, and regeneration, maintaining and promoting the biological activity of many membrane-bound proteins and receptors. PUFA-containing phospholipids also play a decisive role in the activity and activation of numerous membrane-located enzymes, such as sodium-potassium-ATPase, adenylate cyclase, and lipoprotein lipase, are important for the transport of molecules through membranes and control membrane-dependent metabolic processes between the intracellular and intercellular space. Moreover, some PUFAs, such as linoleic acid, are precursors of the cytoprotective prostaglandins and other eicosanoids.

Due to all of their properties, many health benefits have been attributed to the consumption of fatty acids and in particular PUFA. For example, it has been reported that PUFA of the type omega-3 and omega-6 may be effective in the treatment and prevention of cardiovascular disease (CVD).

Besides its benefits with regards to CVD, diabetes and cancer, DHA is also important for enhancement of brain function, and in particular for brain development in infants. Nutritional studies, investigating the importance of DHA in the brain, found that low levels of DHA are associated with depression, memory loss, dementia and visual problems. All studies showed a dramatic improvement in the elderly brain function as blood levels of DHA increased.

The human body does not synthesize DHA in sufficient amounts. Therefore it is necessary to obtain it from the diet. DHA is initially obtained through the placenta, then from breast milk, and later from sources like fish, red meats, animal organ meats and eggs. These types of fatty acids are naturally occurring mainly in fish and algae, where they are randomly distributed on the s7 1, S7X-2, and sn-3 positions of the glycerol backbone of triglycerides. In particular, tuna, salmon and sardines are rich sources.

Furthermore, the ability to enzymatically produce omega-6 and omega-3 products of linoleic and a-a linolenic acid declines with age. Thus, as human beings age, there is an increased need to acquire DHA directly from diet or supplements. Because DHA is important for signal transmission in the brain, eye and nervous system, many consumers concerned with maintaining mental acuity seek for a pure, safe way to supplement their DHA levels. Until recently, the primary source of DHA dietary supplements has been fish oils.

In light of the important physiological roles of phospholipids containing PUFA for human health, and the scarce availability of said compounds in the organism, there is a demand for dietary supplementation of PUFA-containing phospholipids. Many PUFA-containing agents suffer from stability and quality problems due to the high degree of oxidation of the polyunsaturated fatty acids. These problems require the incorporation of antioxidants as well as the utilization of special measures which attempts to reduce this oxidation. The utilization of phospholipids as carriers of PUFA may result in enhanced stability of such products due to the anti-oxidative properties of phospholipids.

PUFA-containing phospholipids may be prepared by various ways, mainly by (i) enzymatic esterification and transesterification of phospholipids, (ii) chemical synthesis of phospholipids, or (iii) enzymatic transphosphatidylation of phospholipids.

It is important to mention that PS is the major acidic phospholipid component in the membranes of the brain. It has been the subject of numerous human clinical trials of memory loss, mood, cognitive performance and learning abilities. Many of the studies show that PS can be helpful for those with age-related memory impairment, and that it can even help optimizing the cognition in those with no cognitive impairment. Dietary PS is efficiently and rapidly absorbed in the intestine, is taken up into the blood, and readily crosses the blood-brain barrier to reach the nerve cells of the brain.

PS can be extracted from bovine brain or from plants, or it can be produced from soybean lecithin using biocatalysis. The main difference between the two sources is the type of fatty acids attached to positions 1 and 2 on the phospholipid skeleton. Long-chain polyunsaturated n-3 type fatty acids are characteristic of marine fat and occur pervasively in the phospholipids of marine species.

Phosphatidylserine can be made by using the transphosphatidylation reaction with phospholipases D (PLDs), by which the head group of phospholipids can be readily modified. Thus, phosphatidylserine can be produced from phosphatidylcholine or any other phospholipid mixture and serine by catalysis with PLD.

Phospholipids are also referred to as lecithins, such as, for example, soybean and egg yolk lecithins, and have long been used in food products, cosmetic products, paints, lubricants, magnetic materials, animal feeds and medicinal and agrochemical products. In this connection, phosphatidyl acid derivatives produced by enzymatic transphosphatidylation from phospholipids and compounds containing hydroxyl groups in some cases show properties superior to those of the starting material.

The structure of the most common class of phospholipids, phosphoglycerides, is based on glycerol, a three-carbon alcohol with the formula $CH_2OH$—$CHOH$—$CH_2OH$. Two fatty acid chains, each typically having an even number of carbon atoms between 14 and 20, attach (via a dual esterification) to the first and second carbons of the glycerol molecule, denoted as the sn1 and sn2 positions, respectively. The third hydroxyl group of glycerol, at position sn3, reacts with phosphoric acid to form phosphatidate. Common phospholipids, widely distributed in nature, are produced by further reaction of the phosphate group in phosphatidate with an alcohol, such as serine, ethanolamine, choline, glycerol, or inositol. The resulting lipids may be charged, for example, phosphatidyl serine (PS), phosphatidyl inositol (PI), and phosphatidyl glycerol (PG); or dipolar (having separate positively and negatively charged regions), for example, phosphatidyl choline (PC), and phosphatidyl ethanolamine (PE). The term "lecithin" refers to PC-type lipids.

A typical phospholipid arrangement is the presence of a saturated fatty acid, such as palmitic or stearic acid, at the sn1 position, and an unsaturated or polyunsaturated fatty acid, such as oleic or arachodonic acid, at sn2 (see FIG. 1 for the structure of a phosphoglyceride).

Another class of phospholipids is the sphingolipids. A sphingolipid molecule has the phosphatidyl-based head-group structure described above, but (in contrast to a common phospholipid molecule) contains a single fatty acid and a long-chain alcohol as its hydrophobic components. Additionally, the backbone of the sphingolipid is sphingosine, an amino alcohol (rather than glyercol). The structure of a representative sphingolipid, sphingomyelin, is also shown in FIG. 1. Sphingolipids, occurring primarily in nervous tissue, are thought to form cholesterol-rich domains within lipid bilayer membranes that may be important to the functions of some membrane proteins.

Phospholipids have many functions in biological systems: as fuels, as membrane structural elements, as signaling agents, and as surfactants. For example, pulmonary surfactant is a mixture of lipids (primarily dipalmitoyl phosphatidyl choline [DPPC]) and proteins that controls the surface tension of the fluid lining of the inner lung (the site of gas exchange), allowing rapid expansion and compression of this lining during the breathing cycle. Phospholipids are the major lipid constituent in cell membranes, thus maintaining structural integrity between the cell and its environment and providing boundaries between compartments within the cell.

Additionally, glycolipids are lipids with a carbohydrate attached by a glycosidic (covalent) bond. Their role is to maintain the stability of the cell membrane and to facilitate cellular recognition, which is crucial to the immune response and in the connections that allow cells to connect to one another to form tissues. Glycolipids are found on the surface of all eukaryotic cell membranes, where they extend from the phospholipid bilayer into the extracellular environment.

Glycolipids encompass a wide variety of compounds: glycosphingolipids (cerebrosides, globosides, gangliosides, sulfatides, and others), glycoglycerolipids, glycophosphospholipids (e.g., phosphatidylinositols), glycosylated prenols (e.g., dolichol-phospho-glycans), glycosylated sterols, glycosylated polyketides, and saccharolipids.

The essential feature of a glycolipid is the presence of a monosaccharide or oligosaccharide bound to a lipid moiety. The most common lipids in cellular membranes are glycerolipids and sphingolipids, which have glycerol or a sphingosine backbones, respectively. Fatty acids are connected to this backbone, so that the lipid as a whole has a polar head and a non-polar tail. The lipid bilayer of the cell membrane consists of two layers of lipids, with the inner and outer surfaces of the membrane made up of the polar head groups, and the inner part of the membrane made up of the non-polar fatty acid tails.

The saccharides that are attached to the polar head groups on the outside of the cell are the ligand components of glycolipids, and are likewise polar, allowing them to be soluble in the aqueous environment surrounding the cell. The lipid and the saccharide form a glycoconjugate through a glycosidic bond, which is a covalent bond. The anomeric carbon of the sugar binds to a free hydroxyl group on the lipid backbone. The structure of these saccharides varies depending on the structure of the molecules to which they bind.

The main function of glycolipids in the body is to serve as recognition sites for cell-cell interactions. The saccharide of the glycolipid will bind to a specific complementary carbohydrate or to a lectin (carbohydrate-binding protein), of a neighboring cell. The interaction of these cell surface markers is the basis of cell recognitions, and initiates cellular responses that contribute to activities such as regulation, growth, and apoptosis.

Glycolipids can modulate membrane organization. They are potential modulators of membrane physical properties They have a number of features that distinguish them from, phospholipids: (i) the ability of hydroxylated sugar head groups to participate in extensive hydrogen bonding both as donors and acceptors, (ii) long and largely saturated acyl chains that promote ordering and interdigitation, (iii) very high main phase transition temperatures compared to corresponding phospholipids, which also supports the view that glycolipids promote order around them. Glycolipids form densely packed lateral domains together with cholesterol and/or sphingomyelin. Glycolipids are playing a main role in cellular membranes. As lipids they are an integral component of lipid membranes, whose physical properties partly dictate the functionality of membrane proteins embedded in membranes.

Representative examples of glycolipids are illustrated in FIG. 2.

The present invention provides improved and more cost-effective methods for the production of omega-3/omega-6 enriched glycerophospholipids and glycolipids.

OBJECTS OF THE INVENTION

Figure 1:
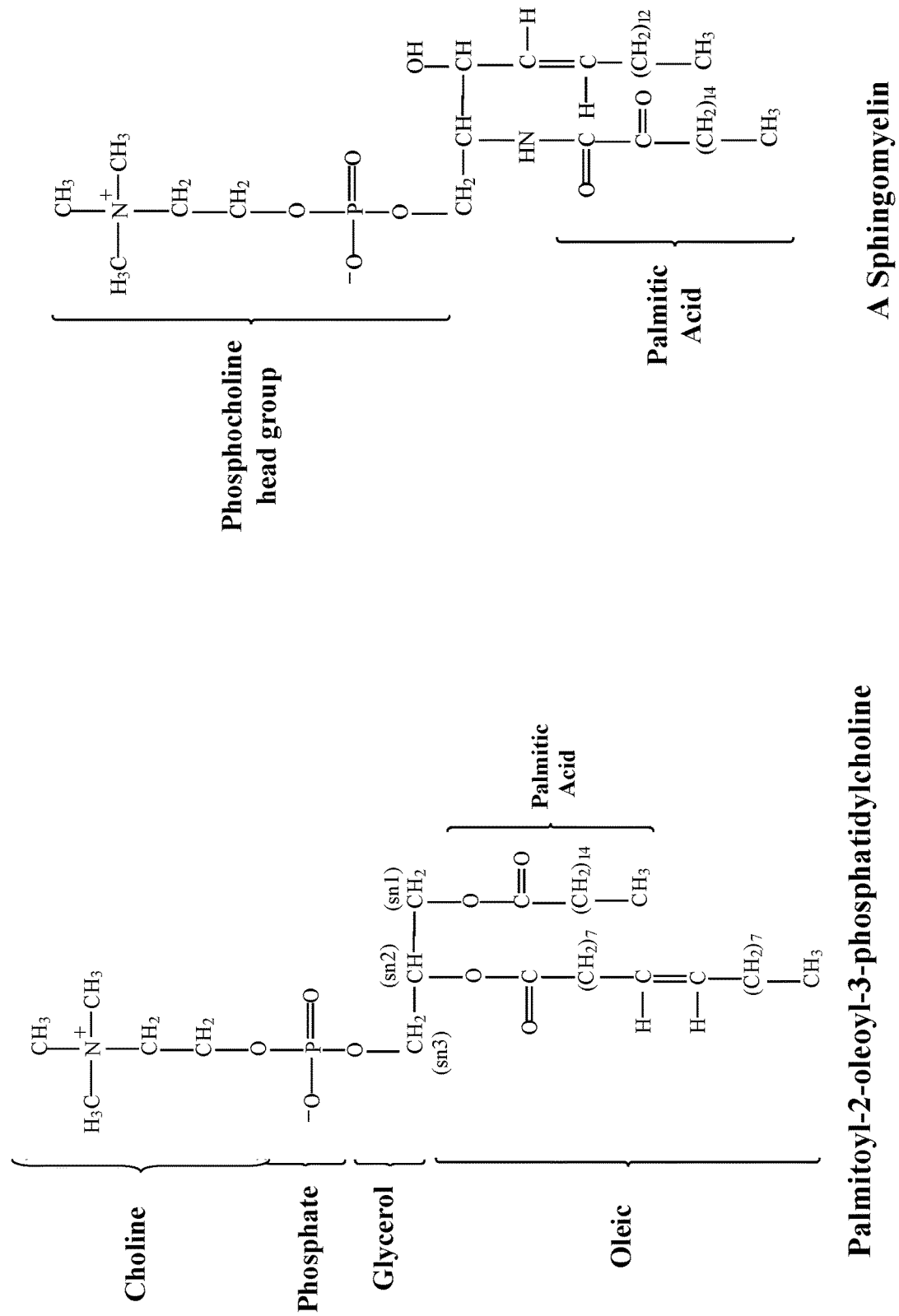
FIG. 1 shows the structure of a phosphoglyceride and a sphingomyelin having fatty acids.
Figure 2:
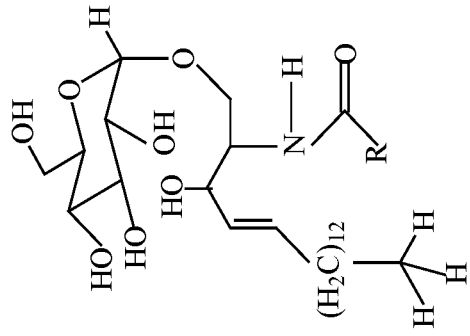
FIG. 2 illustrate chemical structures of glycolipids, glycero-glycolipids and sphingo-glycolipids.
Figure 2:
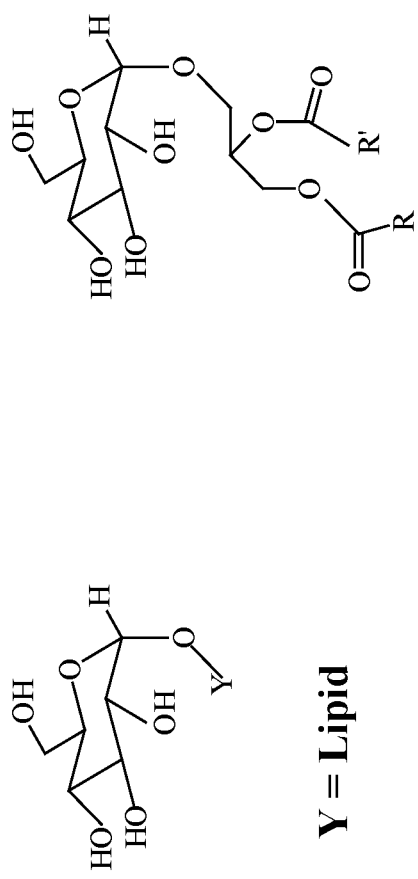

Thus, it is an object of the present invention to provide an improved solventless enzymatic interesterification process for the enrichment of phospholipids with omega-3 and omega-6 fatty acids. The interesterification includes the processes of transesterification of lecithin with omega-3 and 6 fatty acid and esterification process.

It is another object of the present invention to provide solventless enzymatic methods for the production of omega-3 and omega-6 enriched phosphatidylcholine, phosphatidylinositol, phosphatidylserine and phosphatidylethanolamine.

It is a further object of the present invention to provide a method for the production of stabilized phosphatidylserine preparations enriched with omega-3/omega-6 acid residues. In the method presented herein, the production is by solventless enzymatic incorporation of the omega-3 and omega-6 fatty acids by a simple, single step reaction, which can be easily performed on industrial scales.

These and other objects of the invention will become apparent from the foregoing description.

SUMMARY OF THE INVENTION

The invention provides a process for modifying a phospholipid material which comprises exchanging acyl groups in a phospholipid by enzymatic exchange with ethyl esters of omega fatty acids and triacyl glycerols that contain omega-3 fatty acids, the reaction being conducted in the absence of a solvent with an enzymatic system consisting essentially of one or more phospholipases and at a sufficient temperature and for a sufficient time to exchange acyl groups in the phospholipid material and form a modified phospholipid material.

The invention features a process for the incorporation of omega-3 and omega-6 fatty acids into polar lipid molecules present in phospholipids and glycolipids, which process comprises the steps of: (a) conducting an enzymatic exchange reaction between the fatty acids present in the polar lipids of the phospholipids and glycolipds and the omega-3 and omega-6 fatty acids, to obtain an oil with a high content of polar lipids and omega-3 fatty acids and omega-6 fatty acids, (b) a stage of concentration of the polar lipid and omega-3 and omega-6 fatty acids content of the oil obtained in step (a) by supercritical fractionation or molecular distillation; (c) a new feeding stage of concentrated omega-3 oil or omega-6 to increase the incorporation of omega-3 and omega-6 in polar lipids and achieve a higher omega-3 and omega-6 content in the product; and (d) an ultrafiltration stage under a nitrogen atmosphere to give the desired consistency and appearance to the final oil.

The invention also relates to a process for the incorporation of EPA/DHA into polar lipid molecules present in lecithin, which process comprises the following steps: (a) an enzymatic exchange reaction between the fatty acids present in the polar lipids of lecithin and the omega-3 fatty acids present in concentrated fish oil or algae oil, to obtain an oil with a high content of polar lipids and omega-3 fatty acids; (b) a stage of concentration of the polar lipid and omega-3 fatty acids content of the oil obtained in stage a, by supercritical fractionation or molecular distillation; (c) a new feeding stage of concentrated Omega-3 oil (fish or algae) to increase the incorporation of Omega-3 in polar lipids and achieve a higher omega-3 content in the product; and (d) an ultrafiltration stage under a nitrogen atmosphere to give the desired consistency and appearance to the final oil.

The invention further relates to a method for the production of a glycerophospholipid enriched with omega-3 and/or omega-6 fatty acids through enzymatic transesterification, comprising the steps of: (a) reacting in an ultrasonic reactor said glycerophospholipid with an omega-3 and/or omega-6 fatty acid source in the presence of a lipase and/or a phospholipase which can catalyze transesterification at the sn-1 and/or sn-2 positions of the glycerol moiety, for a suitable period of time to give a glycerophospholipid enriched with said omega-3 and/or omega-6 fatty acids at the sn-1 and/or sn-2 positions; (b) removing and filtering the upper layer which contains the enriched glycerophospholipid, in order to separate the glycerophospholipid from the enzyme; and (c) de-oiling using supercritical fluid the filtrate to remove excess FFA.

The invention also provides a softgel capsule incorporating an EPA/DHA enriched phospholipid prepared by enzymatic interesterification in an ultrasonic reactor of phoapholipds containing saturated fatty acids.

DETAILED DESCRIPTION OF THE INVENTION

The present invention provides methods for the preparation of glycerophospholipids enriched with omega-3 and/or omega-6. The methods are essentially methods of enzymatic transesterification and esterification of glycerophospholipids, chemical synthesis, and enzymatic production of phosphatidylserine and other related analogs.

The present invention provides an improved enzymatic interesterification processes for the enrichment of phospholipids with omega 3 and 6 fatty acids. The interesterification includes a process of transesterification of lecithin with omega-3 and 6 fatty acids and an esterification process.

Applicants have developed synthetic pathways that enable the industrial production of the aforementioned phospholipids, which possess unique nutritional and clinical benefits.

The synthetic pathways described herein may be divided into two mam categories:

1. Enzymatic esterification and transesterification of phospholipids with omega-3 and/or omega-6 fatty acids utilizing lipases and phospholipase enzymes.
2. Chemical esterification of phospholipids with omega-3 and omega-6 acyl donors.

The process according to the invention is characterized in that the reaction takes place in the absence of solvent with an enzymatic system consisting of one or more phospholipases. The phospholipases may be immomibilized.

The process of the invention may be applied to any desired kind of phospholipid or glycolipid or sphingomyelin containing fatty acid acyl ester groups. Examples of such naturally occuring phospholipids are lecithin, phosphatidic acid, phosphatidyl choline, phosphatidyl serine, phosphatidyl glycerol, phosphatidyl inositol, phosphatidyl ethanolamine and diphosphatidyl glycerol. Synthetic phospholipids with various hydroxy compounds esterified to the phosphate group, 1-alkyl-2-acyl-phospholipids and diacyl-phospholipids may also be processed.

The exchange reaction may be used to incorporate any desired fatty acid moiety into a phospholipid. Of particular interest are omega-3 fatty acids. All oils and fats containing a significant amount of these fatty acids moieties incorporated in triglycerides may be used as starting materials.

The process of the invention comprises first the manufacture of ethyl ester (EE) concentrated in omega-3, mainly EPA/DHA by means of concentration with molecular distillation of a transesterified fish oil. Then, a treatment process is executed in a column packed with silica for the reduction of saturated, monounsaturated and 18-carbon fatty acids that affect the incorporation process during the subsequent enzymatic reaction.

Once an Ethyl Ester olein is obtained with a low content of saturated fatty acids and $C_{18}$, a chemical reaction can be carried out to saponify the fatty acids using a base (potassium hydroxide, sodium hydroxide or other), and then a splitting using acid (citric, sulfuric, p-toluenesulfonic acid, among others) to obtain free fatty acids (FFA). Additionally, it is possible to perform an enzymatic esterification reaction to EE olein using glycerin and a lipase as a catalyst to obtain omega-3 concentrated triglycerides (TG).

The next stage comprises an enzymatic reaction in which the inputs are fish oil concentrated in omega-3 in chemical form EE, FFA or TG with a lecithin with a high content of polar lipids: phospholipids and glycolipids, which can be soy, rapeseed, sunflower, egg or other of vegetable or animal origin. Taking into account that the chemical form in which omega-3 is found can vary, several reaction mechanisms are considered:

1. Hydrolysis for the breakdown of a fatty acid present in the phospholipid/glycolipid molecule to later carry out an esterification with a n-3 molecule from an FFA, EE or TG.
2. Transesterification of an omega-3 fatty acid from EE with a fatty acid in the SN-1 or SN-2 position of the phospholipid molecule or with the fatty acid present in the glycolipid molecule.
3. Interesterification of an omega-3 fatty acid from TG with a fatty acid in the SN-1 or SN-2 position of the phospholipid molecule or with the fatty acid present in the glycolipid molecule.

The aforementioned enzymatic reactions are carried out in an ultrasonic reactor to favor surface contact and mass transfer, obtaining better yields, high incorporation of omega-3 fatty acids and shorter reaction times compared to conventional mechanical stirring.

The possibility of using different chemical forms in fish oil oleins allows diversifying the reaction mechanisms to be used during incorporation. In turn, products with variations in organoleptic properties are obtained, offering the option of being used in different pharmaceutical and nutraceutical applications as a finished product.

The operating conditions for the reaction would be:
Liquid enzyme: 0.5-10% p/p
Temperature: 30-80° C.
Pressure: 0.01-1013 mbar
Time: 1-48 hours
Water content: 0.1-1%
pH: 2-9
Phospholipid content (PL): 20-60%.
Glycolipid content (GL): 2-10%

The incorporation of omega-3 fatty acids could be carried out in the SN-1 and SN-2 positions of the phospholipid molecule or by replacing the fatty acid present in the glycolipid molecule. This process would be possible through the use of liquid enzymes phospholipases A1 and A2, respectively, which could be added independently (two reaction stages) or in a single dose (one reaction stage).

The use of liquid enzymes avoids the need for a filtration process after the enzymatic reaction to recover the enzyme for use in a next batch. It is important to mention that executing the aforementioned physical separation process requires a special conditioning of the oil to achieve the proper handling of phospholipids. The high molecular weight of the phospholipids and the viscosity of the reaction mixture generates clogging problems, loss of product and high processing time during filtration, having to heat the product to improve its fluidity, however, polyunsaturated fatty acids and EPA/DHA in particular are thermolabile, so heating without proper processing measures will cause oxidation in fatty acid saturations, degrading the molecule. In a second measure, the viscosity of the reaction mixture can be improved using a solvent, however, later a new stage should be added where the solvent is evaporated and recovered from the structured phospholipid. This last option can generate two drawbacks, one from the economic point of view since new equipment must be incorporated into the process, and its operation is reflected in higher production costs. On the other hand, it must be guaranteed that the reaction mixture after evaporation is free of traces of solvents, since depending on the type of solvent used, there could be adverse health effects on the final consumer.

Lecithin contains a mixture of glycolipids, triglycerides, and phospholipids (e.g., phosphatidylcholine, phosphatidylethanolamine, and phosphatidylinositol) and may be derived from natural sources or synthetic sources. Preferably, lecithin for use in the processes of the invention is derived from vegetable sources, such as from soy beans, egg yolks or rapeseed, using conventional processing methods. The phospholipid content of lecithin for use in the processes of the invention is preferably greater than 15% by weight, more preferably greater than 25% by weight, such as greater than 30% by weight. For example, the phospholipid content of lecithin may range from 25 to 60% by weight, such as from 30 to 40% by weight.

Commercial lecithin is an important co-product of oil processing obtained during degumming step. For example, soybean lecithin is a complex mixture and comprises of phospholipids and triglycerides, with minor amounts of other constituents like phytoglycolipids, phytosterols, tocopherols and fatty acids. The major phospholipids present in vegetable lecithins are phosphatidylcholine, phosphatidylethanolamine and phosphatidylinositol. The egg yolk lecithin contains phosphatidylcholine and phosphatidylethanolamine as major phospholipids. Lecithin has potential as a multifunctional additive for food, pharmaceutical and industrial applications. The primary usage of lecithin in food is as an emulsifier.

Lecithin has the following chemical structure:

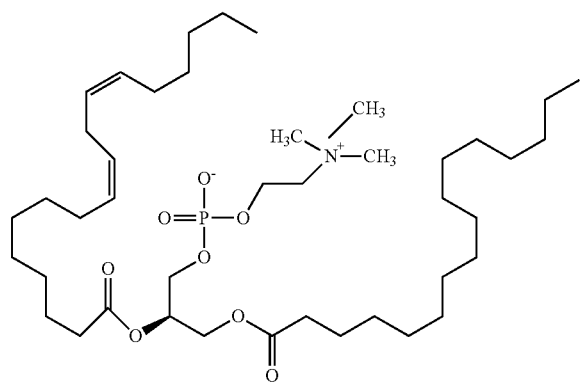

In the process of the invention the fatty acid moieties of lecithin are replaced with omega-3 fatty acid residues such as Docosahexaneoic acid and eicosapentaenoic acid.

The process mentioned in this patent is solvent-free. In other inventions, the use of solvents such as anilines, amines or ethoxides is related to increase the incorporation of polyunsaturated fatty acids in a shorter reaction time. However, using these solvents leads to the efficient evaporation of these components as many are considered toxic and harmful to human health, even in small concentrations.

Therefore, the process of this invention. has multiple benefits compared to the traditional process for the fractionation of phospholipids, which typically uses acetone. Some of them are: i) Products free from organic solvents, ii) Elimination of the stage of solvent recovery, iii) Sharp separation between phospholipids and oils, iv) Creates a sterile environment, v) Deodorizes the oil as well as the phospholipids, vi) Reduces the oxidation and vii) Short residence time.

Depending on the chemical form in which the fish oil concentrated in omega-3 is found, a post-treatment process is carried out. For example, if you start from FFA and EE, once the incorporation of the polyunsaturated fatty acid in the phospholipid/glycolipid molecule is carried out, a multistage molecular distillation could be carried out to increase the polar lipid content from 40% to 90%, separating from FFA and EE due to the difference in volatility and molecular weight of these two molecules with respect to the polar lipid. On the other hand, if the raw material is in the form of TG, the concentration process will be based on the difference in solubility of the TG and the polar lipid in a fluid under supercritical conditions, supercritical fractionation. Discarding molecular distillation due to the high temperatures required for the separation of these two molecules with high molecular weight. For supercritical fractionation, the use of carbon dioxide ($CO_2$) is considered as a supercritical fluid due to its low environmental footprint, high availability, easy recovery and evaporation of the product of interest, low cost and its recognition as GRAS (Generally Recognized As Safe).

Figure 5:
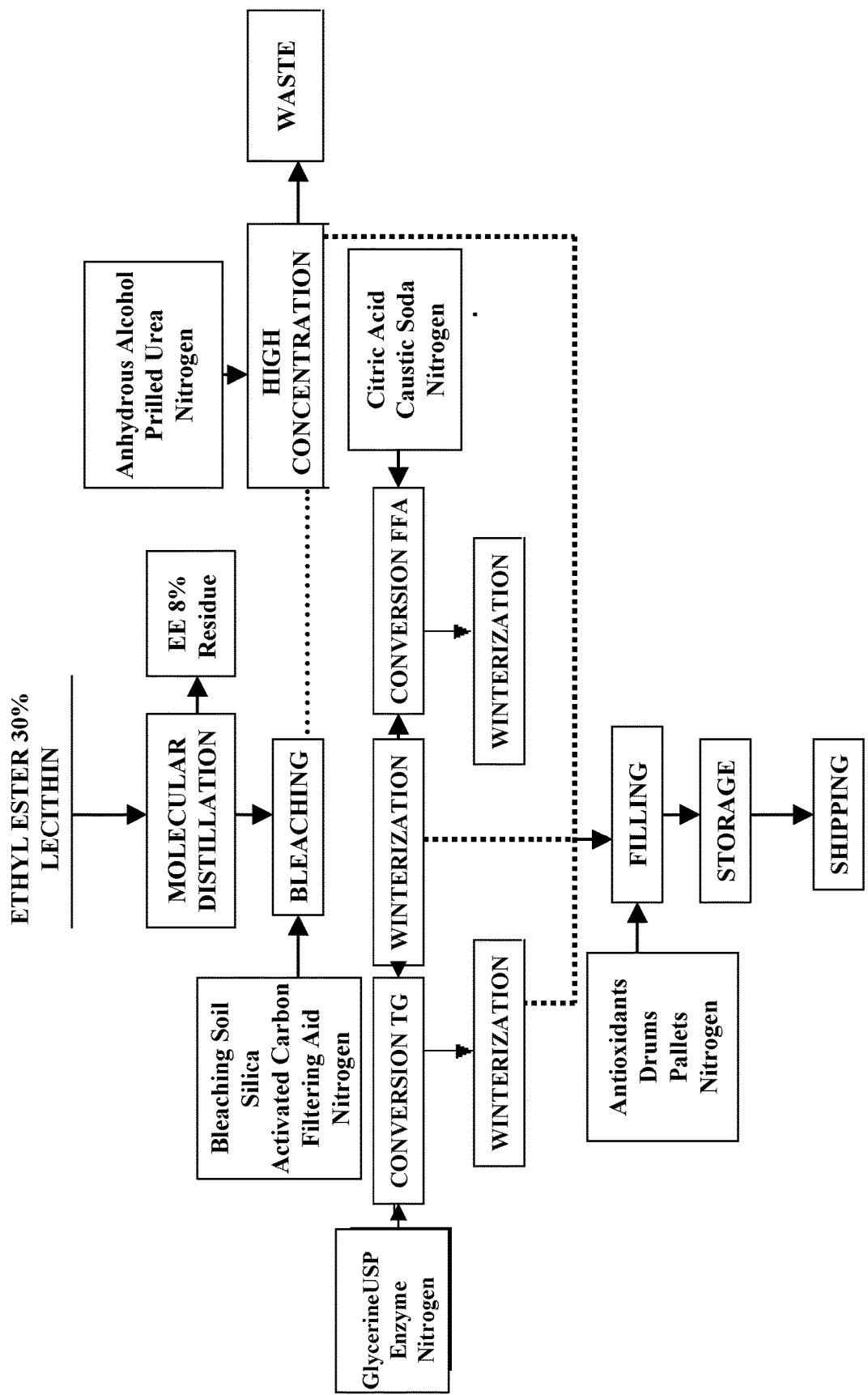
FIG. 5 shows a process diagram of the invention.
Figure 6:
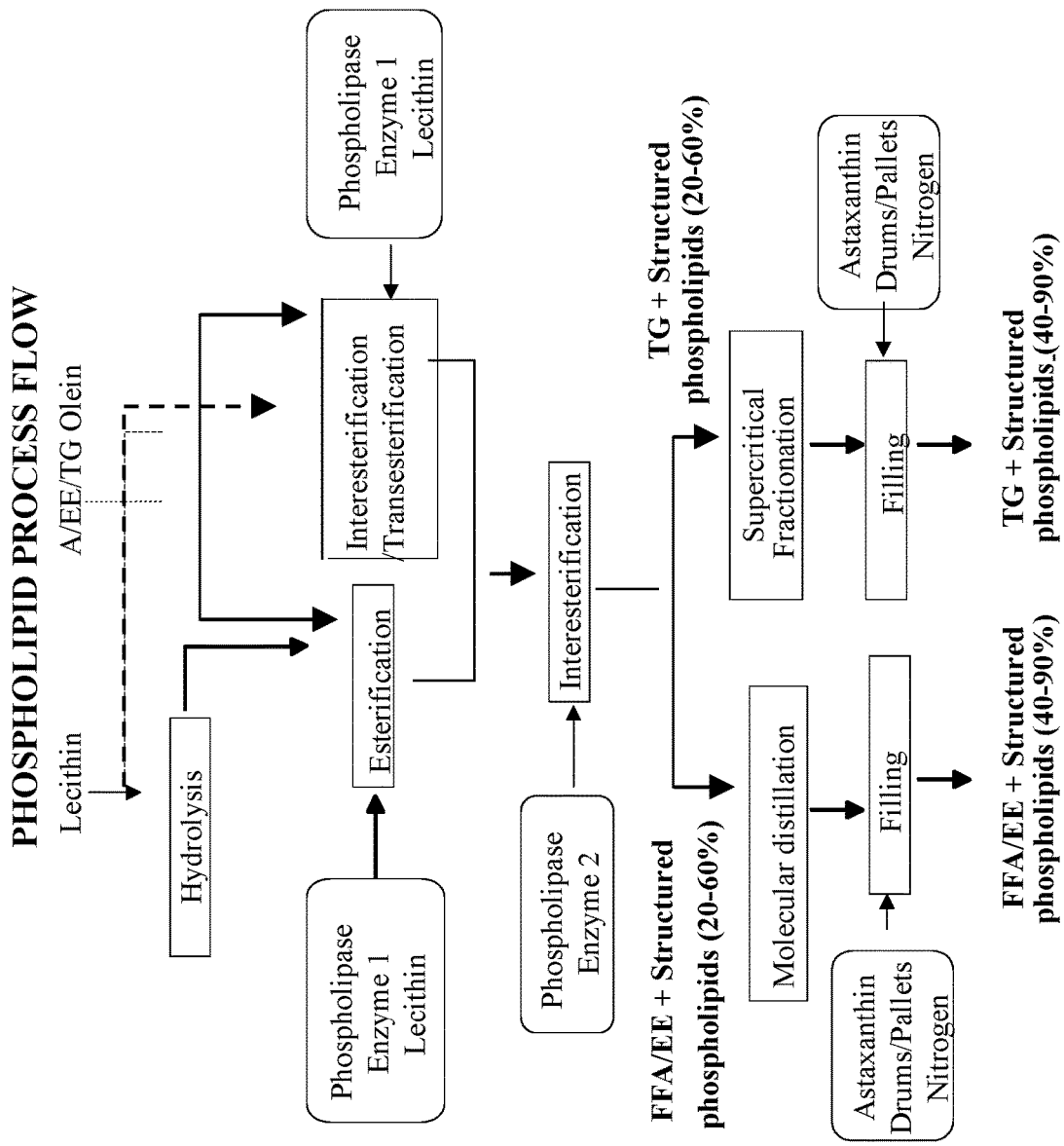
FIG. 6 illustrates the phospholipid process flow of the invention.

The process of this invention uses two types of systems for the concentration of polar lipids and omega 3 fatty acids: batch and continuous. The process flow of the invention are illustrated in FIGS. 5 and 6.

The Batch Process

Figure 3:
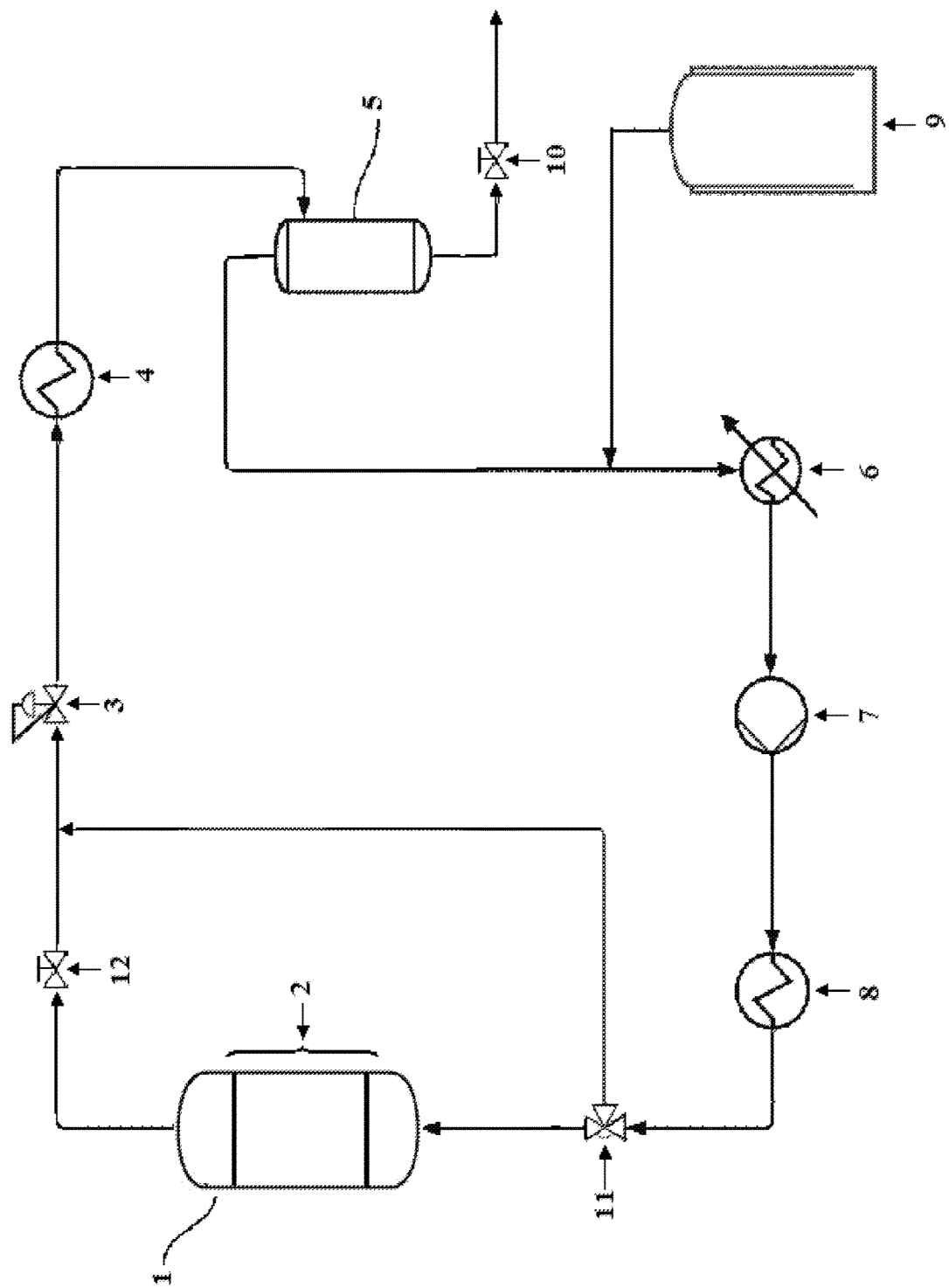
FIG. 3 is a schematic of the batch process of the invention.

In FIG. 3, number 1 depicts an extractor, which can be loaded with a rigid packing, like ceramic, glass or metallic marbles 2, to minimize agglomeration of the phospholipids and facilitate deoiling during the extraction process. To the extractor is added the Ruby-O, in ethyl ester or triglycerides form, although ethyl ester is preferred, due to its higher solubility in supercritical $CO_2$(SC—$CO_2$). Ruby-O typically consists of 40-50% acetone insoluble matter (AI). $CO_2$ flowrate is first regulated by using the two-way switching valve 11 to bypass the extractor and closing valve 12. Once stable flowrate is achieved, to the extractor is fed supercritical CO2 from the bottom, by switching the two-way valve 11 and opening the manual valve 12, at temperatures between 40 and 80° C. and pressures between 10 and 70 MPa. The solvent is passed through the extraction cell 1 and exits at the top, loaded with oil. The SC—CO2 is expanded in a backpressure regulator valve 3 to pressures between 5 and 7 MPa and passed through a water heating bath 4 before going to a separation vessel 5.

The separation vessel 5 has two exits, one at the top where CO2 gas leaves free of oil and goes to a condenser 6 and a high-pressure reciprocating pump 7. The liquid $CO_2$ is pumped at the extraction working pressure and heated to the working temperature in a water heating bath 8. The $CO_2$ leaves the heater 8 in the supercritical state and is fed back to the extractor 1. The oil extracted from Ruby-O is drained from the separation vessel 5 through manual valve 10. The $CO_2$ dissolved in the oil that is lost during drainage is replaced with $CO_2$ fed before the condenser 6 from gas deposit 9.

The Continuous Process

Figure 4:
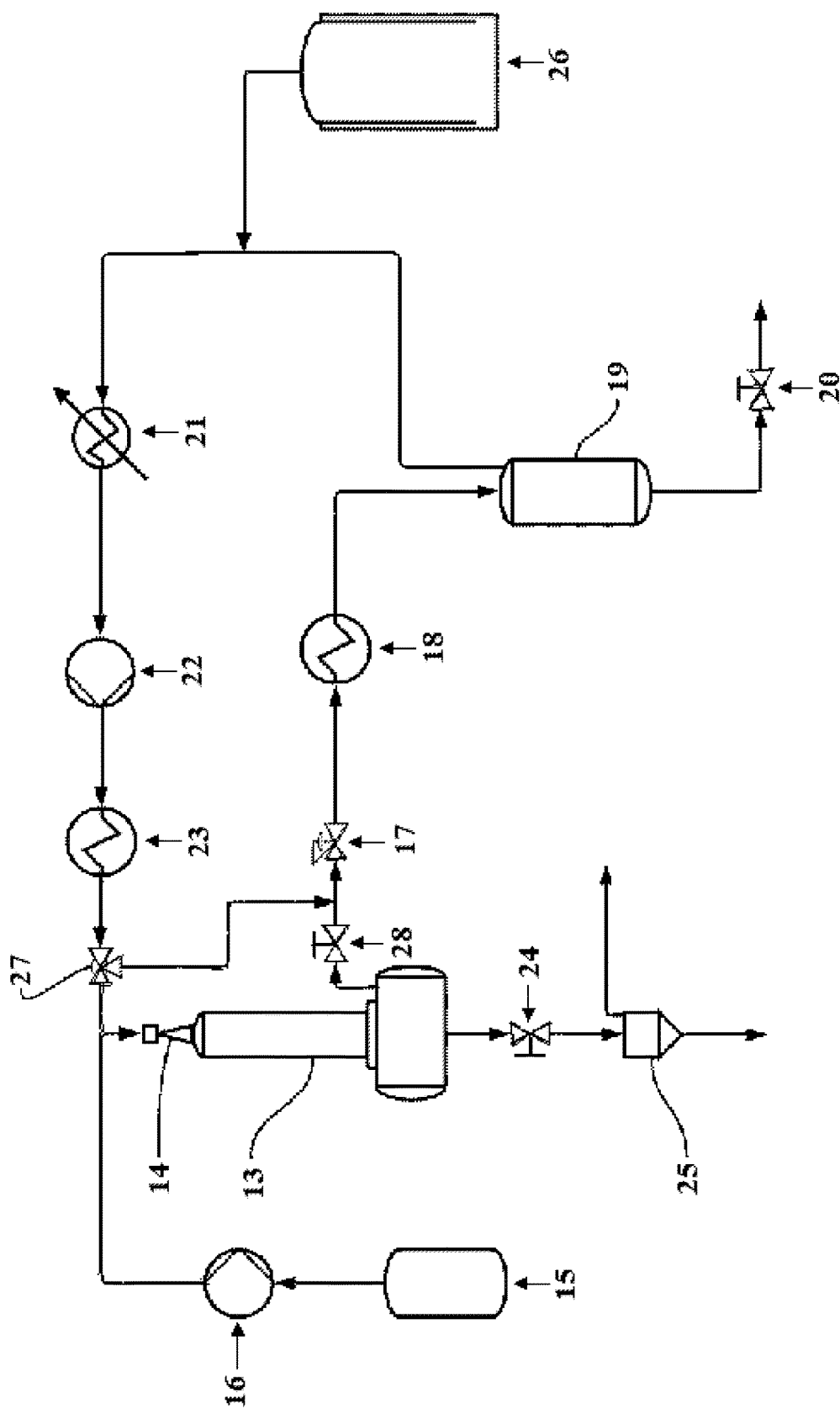
FIG. 4 features a schematic of the continuous process of the invention.

The process for continuous extraction of oil from Ruby-O is depicted in FIG. 4. Herein, the Ruby-O is preheated between 30 and 80° C. in the storage tank 15 and pumped to a pressure higher than the extraction pressure by a reciprocating pump 16. The Ruby-O is mixed with supercritical $CO_2$ and sent through a nozzle 14 to create a jet of highly dispersed Ruby-O, therefore increasing the area available for mass transfer. Working pressures are between 10 and 70 MPa and working temperatures are between 30 and 80° C. The jet passes through an extraction column 13 where oil is dissolved in CO2 and then taken out of the column through an outlet in the bottom accumulator. Meanwhile, Ruby-O falls as powdery particles into the accumulator. Before the column there is a two-way switching valve 27 used to bypass the extraction column 13, principally during the start of the operation, where $CO_2$ flowrate is not stable.

The separation vessel 19 has two exits, one at the top where $CO_2$ gas leaves free of oil and goes to a condenser 21 and a high-pressure reciprocating pump 22. The liquid $CO_2$ is pumped at a pressure slightly higher than the extraction working pressure and heated to the working temperature in a water heating bath 23. The $CO_2$ leaves the heater 23 in the supercritical state and is mixed with the Ruby-O before passing through the nozzle 17. The oil extracted from Ruby-O is drained from the separation vessel 19 through manual valve 20. The oil-free Ruby-O is taken out of the accumulator through a manual valve 24 and expanded into a cyclone separator 25. The Ruby-O powder is obtained at the bottom of the cyclone 25 and the $CO_2$ is lost to the atmosphere. The $CO_2$ dissolved in the oil that is lost during drainage is replaced with $CO_2$ fed before the condenser 21 from gas deposit 26.

The process of the invention may be applied to any desired kind of phospholipd, glycerophospholipid or glycolipd containing a fatty acyl ester group in the sn-2 position, particularly to 1-alkyl-2-acyl-phospholipid (etherphospholipid) and to diacyl-phospholipid.

Suitable phopholipids for carrying out the process of the invention are selected from the group consisting of: lecithin, phosphatidic acid, phosphatidyl choline, phosphatidyl serine, phosphatidyl glycerol, phosphatidyl inositol, phosphatidyl ethanolamine and diphosphatidyl glycerol and synthetic phospholipids with various hydroxy compounds esterified on the phosphate group, 1-alkyl-2-acyl-phospholipids and diacyl-phospholipids.

Suitable glycolipids for carrying out the process of the invention are selected from the group consisting of: glycoglycerolipids, galactolipids, sulfolipids, glycosphingolipids, cerebrosides, galacto-cerebrosides, glucocerebrosides, sulfatides, gangliosides, globosides, glyco-phosphosphingolipids, phytoglycolipids, glycophosphatidylinositols and saccharolipids.

The exchange reaction of the invention may be used to incorporate any desired fatty acid into a phospholipid. Some examples of fatty acids that may be of particular interest are:

Long-chain ($C_{18}$-$C_{22}$) polyunsaturated fatty acid, such as linoleic, arachidonic, α-linolenic, eicosapentaenoic, docosahexaenoic, docosapentanoic or γ-linolenic acids. These may be incorporated to improve the physiological or nutritional value of the phospholipid, especially a diacyl-phospholipid. These may be incorporated to modify emulsification properties, to modify the physiological value or to improve oxidation stability of a phospholipid, especially a diacyl-phospholipid.

Preferred omega-3 fatty acids are selected from the group consisting of: α-linolenic acid, eicosapentaenoic acid, and docosahexaenoic acid.

Preferred omega-6 fatty acid is selected from the group consisting of: linoleic acid, arachidonic acid, γ-linoleic acid and conjugated linoleic acid.

The enzyme catalyst to be used comprises a phospholipase which may be of animal, plant or microbial origin and may be positionally non specific or specific, e. g., preferably an extracellular phospholipase A2, e. g. Lecitase™, Novo Nordisk a/s.

The enzymes used in the process of the invention may be used by themselves or immobilized on a particulate macroporous organic or inorganic carrier, and are preferably attached to the carrier by cross-linking with any suitable cross-linking agent, e. g. glutaraldehyde.

The phospholipase is chosen so that the phospholipase represents 25 to 100% and preferably 30 to 70% by weight of the total enzyme, which is also the same percentage of the total activity of the enzyme system.

The interesterifying process should be carried out under conditions in which optimal activity and thermostability of the enzymes are given, preferable at 60-80° C. and for 1 to 72 h, preferably for about 23 h. At the end of the reaction, the enzymes are separated, e. g. by filtering. One advantage of the present method is that, when it is necessary, the phospholipids can easily be separated from the triglycerides.

In case of any other triglyceride being used and a separation is desired, the classical lecithin purification methods, such as acetone fractionation or degumming, e. g. with about 0.3% phosphoric acid at about 90° C. can be applied. As an alternative, which is not preferred, the separation can take place by high performance thin layer chromatography (HPTLC).

The modified lecithins obtained by the process of the invention may be used in many food and pharmaceutical applications.

Finally, the addition and mixing of the antioxidant agent, astaxanthin, is carried out. The key embodiments of the invention are:

EPA content in the phospholipid molecule between 5-70% considering the SN-1 and SN-2 positions. If the SN-1 position is considered, the EPA concentration would be between 5-35%, and in the SN-2 position it would be between 5-35%.

DHA content in the phospholipid molecule between 5-70% considering the SN-1 and SN-2 positions. If the SN-1 position is considered, the EPA concentration would be between 5-35%, and in the SN-2 position it would be between 5-35%.

At least 90% of the phospholipid molecules will have an omega-3 fatty acid incorporated.

A process of removal of saturated, monosaturated and 18-carbon fatty acids is carried out through a column packed with silica. This would allow the reduction of impurities and greater incorporation of polyunsaturated fatty acids in the phospholipid.

Enzymatic reaction mechanisms with ultrasound that include: hydrolysis, transesterification, esterification and interesterification.

The molecular forms of phospholipids to take into account are: phosphatidylcholine, phosphatidylserine, phosphatidylethanolamine, phosphatidylinositol, phosphatidic acid, among others.

The enzymatic reaction does not use a solvent.

For the enzymatic reaction, a liquid lipase or phospholipase enzyme (a chimera produced by the fusion of the genes of the lipase from *Thermomyces lanuginosus* and the phospholipase A1 from *Fusarium oxysporum* also known by the tradename Lecitase Ultra from Novozymes, Phospholipase C also known by the tradename Purifine from DSM and *Candida antarctica* lipase B also known by the tradename CALB from Novozymes) of any origin (plant, animal and/or microbial) will be used.

The phospholipid content in the enzymatic reaction mixture obtained can vary between 20 and 60%.

The phospholipid content after post-treatment with molecular distillation or supercritical fractionation can vary between 40 and 90%.

It uses molecular distillation as a technology for the concentration of phospholipids obtained with FFA or EE raw materials. On the other hand, supercritical fractionation is used for the concentration of phospholipids in a mixture with TG, due to the high molecular weight of both components., which is why the concept of solubility is used for the separation of PLs.

The products of the invention include compositions illustrated in the tables below.

TABLE 1

Enriched phospholipids/glycolipids containing EPA and DHA

| TYPE OF PRODUCT/ CHARACTERISTICS | RUBY- O CONCENTRATED PHOSPHOLIPID & GLYCOLIPID OMEGA-3 42/45 [%] | RUBY- O CONCENTRATED PHOSPHOLIPID OMEGA-3 42/35 [%] | [%] |
|---|---|---|---|
| Phospholipids (g/100 g) [%] | 35 | 35 | 20-90 |
| Glycolipids (g/100 g) [%] | 7 | 7 | 2-20 |
| Phosphatidylcholine (g/100 g) [%] | 20 | 20 | 10-65 |
| C20:5n3 - Eicosapentaenoic Acid (A %) | 5 | 17 | 5-70 |
| C22:6n3 - Docosahexaenoic Acid (A %) | 35 | 13 | 5-70 |
| Total Omega 3 (A %) | 45 | 35 | 5-90 |
| C20:5n3 - Eicosapentaenoic Acid (TG) (%) | 4.2 | 16 | 4-80 |
| C22:6n3 - Docosahexaenoic Acid (TG) (%) | 26 | 11 | 4-80 |
| Total Omega 3 (TG) (%) | 30 | 32 | 5-90 |
| Astaxanthin (%) | 0.03 | 0.03 | 0.01-0.05 |

1. Products based on soy lecithin and fish oil where we can find different concentrations of Omega-3 that allow to give a specific application to each reference, some examples are shown below:

TABLE 2

Omega-3 phospholipids (40/32) Balance
Soy lecithin/Softgel - 1000 mg

| PARAMETERS | BALANCE (40/32) |
|---|---|
| Glycolipids [mg] | 50 |
| Phospholipids [mg] | 350 |
| Phosphatidylcholine [mg] | 150 |
| Phosphatidyletanolamine [mg] | 50 |
| Phosphatidylinositol [mg] | 40 |
| Phosphatic Acid + Others PL [mg] | 50 |
| C20:5n3 - Eicosapentaenoic Acid (TG) [mg] | 160 |
| C22:6n3 - Docosahexaenoic Acid (TG) [mg] | 110 |
| EPA in phospolipids [A %] | 24 |
| DHA in Phospholipis [A %] | 16 |
| EPA+DHA (TG) mg | 270 |
| Total Omega 3 (TG) [mg] | 320 |
| Docosapentaenoic acid [mg] | 20 |
| Astaxanthin [mcg] | 300 |
| Cholesterol [mg] | 5 |
| Phytosterols [mg] | 7 |

TABLE 3

Omega-3 phospholipids (40/32) by functionality
Soy lecithin/Softgel - 1000 mg

| TYPE OF PRODUCT/CHARACTERISTICS | NEURO (40/35) | CARDIO (40/32) | VISION/ PRENATAL (40/32) |
|---|---|---|---|
| Glycolipids [mg] | 50 | 50 | 50 |
| Phospholipids [mg] | 350 | 350 | 350 |
| Phosphatidylcholine [mg] | 150 | 150 | 150 |
| Phosphatidyletanolamine [mg] | 50 | 50 | 50 |
| Phosphatidylinositol [mg] | 40 | 40 | 40 |
| Phosphatic Acid – Others PL [mg] | 50 | 50 | 50 |
| C20:5n3 - Eicosapentaenoic Acid (TG) [mg] | 42 | 180 | 50 |
| C22:6n3 - Docosahexaenoic Acid (TG) [mg] | 260 | 90 | 250 |
| EPA + DHA (TG) mg | 302 | 270 | 300 |
| Total Omega 3 (TG) [mg] | 350 | 320 | 320 |
| Docosapentaenoic acid [mg] | 20 | 20 | 20 |
| Astaxanthin [mcg] | 300 | 300 | 300 |
| Cholesterol [mg] | 5 | 5 | 5 |
| Phytosterols [mg] | 7 | 7 | 7 |

2. A line of "Soy Free" products, based on sunflower lecithin and fish oil, which are shown in Table 4.

TABLE 4

Omega-3 phospholipids "Soy Free"
Sunflower Lecithin/Softgel - 1000 mg

| PARAMETERS | BALANCE (40/32) Soy Free | NEURO (40/35) Soy Free | CARDIO (40/32) Soy Free | VISION/ PRENATAL (40/32) Soy Free |
|---|---|---|---|---|
| Glycolipids [mg] | 50 | 50 | 50 | 50 |
| Phospholipids [mg] | 350 | 350 | 350 | 350 |
| Phosphatidylcholine [mg] | 100 | 100 | 100 | 100 |
| Phosphati dyl etanol amine [mg] | 44 | 44 | 44 | 44 |
| Phosphatidylinositol [mg] | 72 | 72 | 72 | 72 |
| Phosphatic Acid + Others PL [mg] | 68 | 68 | 68 | 68 |
| C20:5n3 - Eicosapentaenoic Acid (TG) mg/g | 160 | 42 | 180 | 50 |
| C22:6n3 - Docosahexaenoic Acid (TG) [mg] | 110 | 260 | 90 | 250 |
| EPA + DHA (TG) mg | 270 | 302 | 270 | 300 |
| Total Omega 3 (TG) [mg] | 320 | 350 | 320 | 320 |

TABLE 4-continued

Omega-3 phospholipids "Soy Free"
Sunflower Lecithin/Softgel - 1000 mg

| PARAMETERS | BALANCE (40/32) Soy Free | NEURO (40/35) Soy Free | CARDIO (40/32) Soy Free | VISION/ PRENATAL (40/32) Soy Free |
|---|---|---|---|---|
| Docosapentaenoic acid [mg] | 20 | 20 | 20 | 20 |
| Astaxanthin [mcg] | 300 | 300 | 300 | 300 |
| Cholesterol [mg] | 5 | 5 | 5 | 5 |
| Phytosterols [mg] | 7 | 7 | 7 | 7 |

3. A "Plant Based" product, made from algae oil and soy lecithin; its characteristics are shown in Table 5.

TABLE 5

Omega-3 phospholipids "Plant Based"
Soy Lecithin Algae Oil/ Softgel - 1000 mg

| PARAMETERS | Plant based |
|---|---|
| Glycolipids [mg] | 50 |
| Phospholipids [mg] | 350 |
| Phosphatidylcholine [mg] | 150 |
| Phosphatidyletanolamine [mg] | 50 |
| Phosphatidylinositol [mg] | 40 |
| Phosphatic Acid + Others PL [mg] | 50 |
| C20:5n3 - Eicosapentaenoic Acid (TG) [mg] | 0 |
| C22:6n3 - Docosahexaenoic Acid (TG) [mg] | 270 |
| EPA + DHA (TG) mg | 270 |
| Docosapentaenoic acid [mg] | 60 |
| Astaxanthin [mcg] | 300 |
| Cholesterol [mg] | 5 |
| Phytosterols [mg] | 7 |

4. A product with a higher concentration of Omega-3, obtained using supercritical fluid extraction technology, which offers the possibility of reaching Omega-3 concentrations such as those listed in Table 6.

TABLE 6

Omega -3 phospholipids processed by SFE

| | Omega- 3 Phospholipids | | |
|---|---|---|---|
| | Before | After | Final product |
| Acid Value (mg KOH/g) | 14.06 | 0.28 | 0.30 |
| Peroxide (meq/kg) | 0.84 | 0.67 | 0.60 |
| Moisture (%) | 0.6534 | 0.0327 | 0.0213 |
| Acetone Insolubles (%) | 45 | 98 | 49 |
| EPA (mg/g) | 177 | 165 | 241 |
| DHA (mg/g) | 130 | 112 | 176.5 |

The product shown in table 6 was obtained by the batch process, described below:

A batch extractor was loaded with 400 g of Omega-3 phospholipids obtained by enzymatic reaction, it has a content of 45% acetone insoluble matter and 55% oil, and 177 mg/g of EPA and 130 mg/g of DHA. The oil was composed of 93% ethyl esters and the remaining 7% is a mixture of glycerides. The extractor was heated to 40° C. and kept at this temperature during the whole extraction process. $CO_2$ flowrate was adjusted to 295 g/min by using the two-way switching valve to bypass the extractor. Once the flowrate was stable, $CO_2$ was fed to the extractor. The extraction process began when the pressure reached 20 MPa and was left to continue for 1 hour, draining the separator every 10 min; after 45 minutes no more oil was extracted. The extractor was emptied and washed with hexane when needed to fully remove the powdered Omega-3 phospholipids. The hexane was removed using a rotary evaporator. This product was mixed with a high EPA oil with 60% triglycerides in a 1:1 ratio by weight. A new step of enzymatic interesterification is carried out for obtaining a final product with more Omega-3 present even in the polar lipid molecule.

Figure 7:
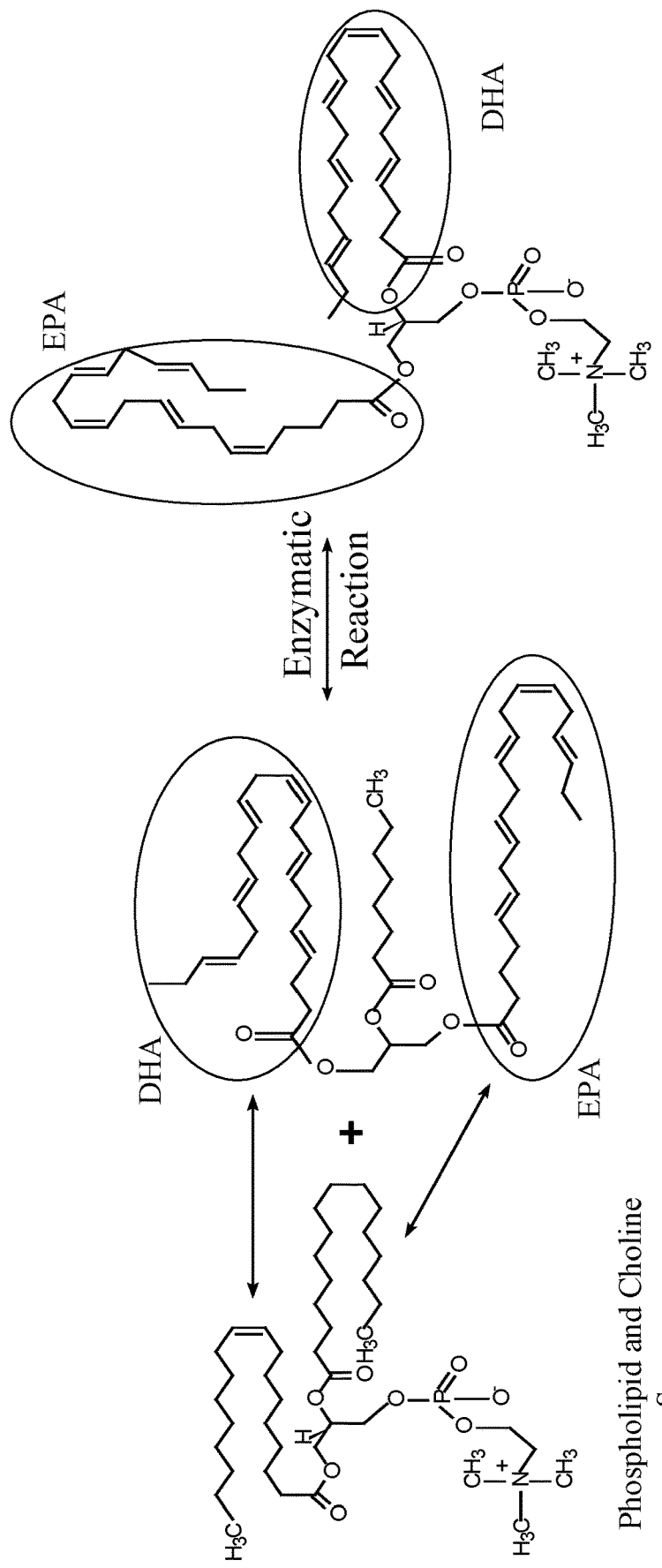
FIG. 7 describes structurally the enzymatic incorporation of EPA and DHA into the phospholipid to make a concentrated phospholipid.
Figure 8:
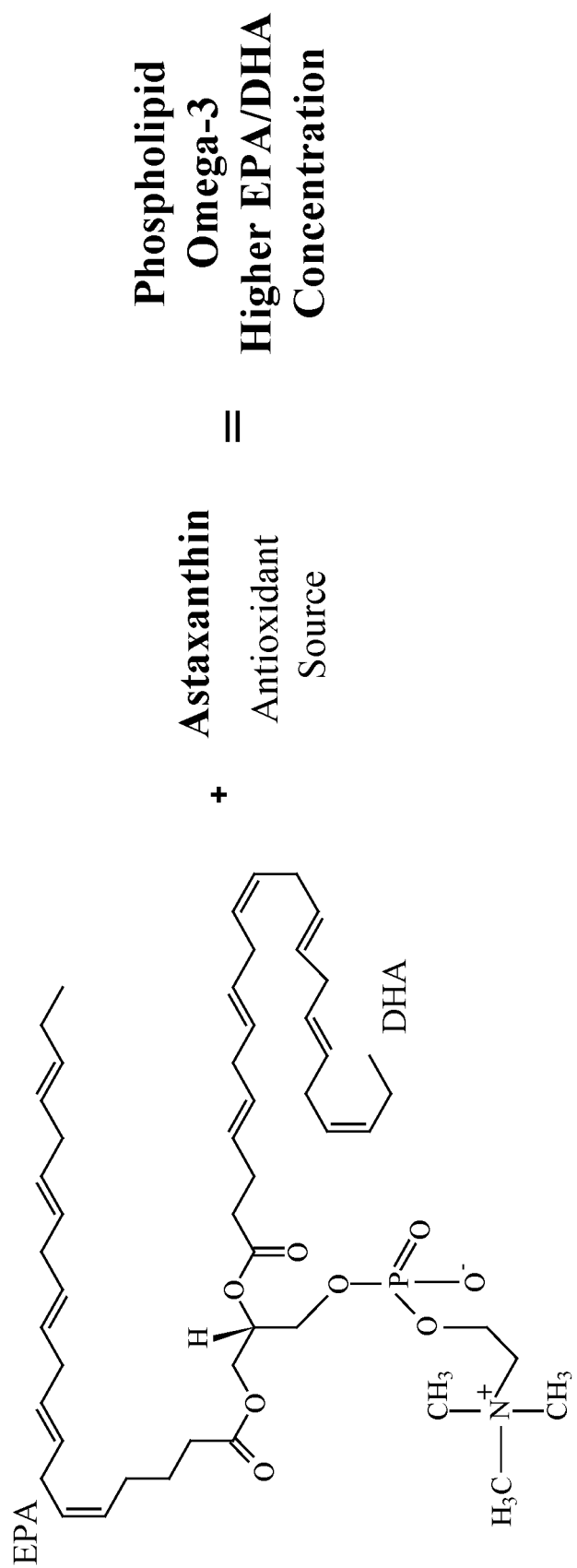
FIG. 8 features the final product of the invention treated with the antioxidant astaxanthin.

The diagrams of FIGS. 7 and 8 illustrate the enriched products of the invention.

The products of the invention are usable in emulsification of lipid drug delivery systems which has demonstrated advantages for improving bioavailability, and the absorption of omega-3 in the body since the emulsification reduces the size of the oil droplet and increases the contact area between oil and water.

All literature and similar materials cited in this application including, but not limited to, patents, patent applications, articles, books, treatises, and internet web pages, regardless of the format of such literature and similar materials, are expressly incorporated by reference in their entirety for any purpose as if they were entirely denoted. In the event that one or more of the incorporated literature and similar materials defines or uses a term in such a way that it contradicts that term's definition in this application, this application controls.

Although the foregoing description contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletions and modifications to the invention as disclosed herein which fall within the meaning and scope of the claims are to be embraced thereby.

What is claimed is:

1. A process for the incorporation of omega-3 and omega-6 fatty acids into polar lipid molecules present in phospholipids and glycolipids, which process comprises the steps of: (a) conducting an enzymatic exchange reaction between the fatty acids present in the polar lipids of the phospholipids and glycolipds and the omega-3 and omega-6 fatty acids, to obtain an oil with a high content of polar lipids and omega-3 fatty acids and omega-6 fatty acids, said enzymatic exchange reaction being conducted in the presence of a lipase or phospholipase enzyme selected from the group consisting of a chimera produced by the fusion of the genes of the lipase from *Thermomyces lanuginosus* and the phospholipase A1 from *Fusarium oxysporum* (Lecitase Ultra), Phospholipase C (Purifine), and *Candida antarctica* lipase B (CALB); (b) a stage of concentration of the polar lipid and omega-3 and omega-6 fatty acids content of the oil obtained in step (a) by supercritical fractionation or molecular distillation; (c) a new feeding stage of concentrated omega-3 oil or omega-6 to increase the incorporation of omega-3 and omega-6 in polar lipids and achieve a higher omega-3 and omega-6 content in the product; and (d) an ultrafiltration stage under a nitrogen atmosphere to give the desired consistency and appearance to the final oil.

2. The process of claim 1, wherein said phopholipid is selected from the group consisting of: lecithin, phosphatidic acid, phosphatidyl choline, phosphatidyl serine, phosphatidyl glycerol, phosphatidyl inositol, phosphatidyl ethanolamine and diphosphatidyl glycerol and synthetic phospholipids with various hydroxy compounds esterified on the phosphate group, 1-alkyl-2-acyl-phospholipids and diacyl-phospholipids.

3. The process of claim 1, wherein said glycolipids are selected from the group consisting of: glycoglycerolipids, galactolipids, sulfolipids, glycosphingolipids, cerebrosides, galacto-cerebrosides, glucocerebrosides, sulfatides, gangliosides, globosides, glycophosphos-phingolipids, phytoglycolipids, glycophosphatidylinositols and saccharolipids.

4. The process of claim 1, wherein said omega-3 fatty acid is selected from the group consisting of: α-linolenic acid, eicosapentaenoic acid, and docosahexaenoic acid.

5. The process of claim 4, wherein said omega-3 fatty acid is selected from the group consisting of eicosapentaenoic acid, docosahexaenoic acid and mixtures thereof.

6. The process of claim 5, wherein said omega-3 fatty acids are selected from the group consisting of eicosapentaenoic acid, docosahexaenoic acid and mixtures thereof and wherein said omega-3 fatty acids are derived from concentrated fish oil or algae oil.

7. The process of claim 1, wherein said omega-6 fatty acid is selected from the group consisting of: linoleic acid, arachidonic acid, γ-linoleic acid and conjugated linoleic acid.

8. The process of claim 1, wherein said enzymatic exchange reaction is conducted in an ultrasonic reactor.

9. The process according to claim 1 in which the enzymatic exchange reaction is carried out in the absence of solvent or added solvents.

10. The process according to claim 1, in which the enzymatic exchange reaction uses liquid enzymes and said lipases or phospholipases are obtained from plant, animal, and/or microbial origin.

11. The process according to claim 6, wherein the concentrated fish oil can be in the form of free fatty acids (FFA), ethyl ester (EE) or triglycerides (TG).

12. The process according to claim 1, wherein the enzymatic exchange reaction includes transesterification, esterification or interesterification.

13. The process of claim 12, wherein the interesterifying process is conducted under conditions in which optimal activity and thermostability of the enzymes are preserved, at a temperature range of 60-80° C. and for 1 to 72 hours, and for about 23 hours.

14. A process for the incorporation of EPA/DHA into polar lipid molecules present in lecithin, which process comprises the following steps: (a) an enzymatic exchange reaction between the fatty acids present in the polar lipids of lecithin and the omega-3 fatty acids present in concentrated fish oil or algae oil, to obtain an oil with a high content of polar lipids and omega-3 fatty acids, said enzymatic exchange reaction being conducted in the presence of a lipase or phospholipase enzyme selected from the group consisting of a chimera produced by the fusion of the genes of the lipase from *Thermomyces lamiginosus* and the phospholipase A1 from *Fusarium oxysporum* (Lecitase Ultra), Phospholipase C (Purifine), and *Candida antarctica* lipase B (CALB); (b) a stage of concentration of the polar lipid and omega-3 fatty acids content of the oil obtained in stage a, by supercritical fractionation or molecular distillation; (c) a new feeding stage of concentrated Omega-3 oil (fish or algae) to increase the incorporation of Omega-3 in polar lipids and achieve a higher omega-3 content in the product; and (d) an ultrafiltration stage under a nitrogen atmosphere to give the desired consistency and appearance to the final oil.

\* \* \* \* \*